US006744373B2

(12) United States Patent
Koyano et al.

(10) Patent No.: US 6,744,373 B2

(45) Date of Patent: Jun. 1, 2004

(54) PORTABLE GAS ALARM DEVICE

(75) Inventors: Junichi Koyano, Tokyo (JP); Shuji Tajima, Tokyo (JP); Yoshiharu Ao, Tokyo (JP); Masahide Kitamura, Tokyo (JP)

(73) Assignee: Riken Keiki Co., Ltd., Tokyo (JP)

(*) Notice: Subject to any disclaimer, the term of this patent is extended or adjusted under 35 U.S.C. 154(b) by 0 days.

(21) Appl. No.: 10/105,597

(22) Filed: Mar. 25, 2002

(65) Prior Publication Data

US 2003/0052792 A1 Mar. 20, 2003

(30) Foreign Application Priority Data

Sep. 17, 2001 (JP) ....................................... 2001-281953

(51) Int. Cl.[7] ........................ G08B 17/10; G08B 23/00; G01N 33/497; G01N 27/62; G01R 31/08

(52) U.S. Cl. .................... 340/693.5; 340/628; 340/632; 340/970; 73/23.2; 73/23.31; 73/31.02; 324/464; 324/465; 324/514

(58) Field of Search ................................ 340/628, 629, 340/630, 632, 693.5, 691.5, 970, 977, 521, 573.1; 73/23.2, 31.02, 23.31; 324/464, 465, 514

(56) References Cited

U.S. PATENT DOCUMENTS 4,384,283 A * 5/1983 Drope et al. ................ 205/775
4,665,385 A * 5/1987 Henderson ............. 340/539.26
6,388,576 B1 * 5/2002 Liu et al. ..................... 340/576
6,411,207 B2 * 6/2002 Shaffer ........................ 340/521
6,426,703 B1 * 7/2002 Johnston et al. ............ 340/628
6,452,510 B1 * 9/2002 Zysko ......................... 340/970
6,606,897 B1 * 8/2003 Koyano et al. .............. 73/23.2

FOREIGN PATENT DOCUMENTS

DE 296 01 472 U1 5/1996
GB 2331363 A * 5/1999 .......... G01N/27/00

* cited by examiner

*Primary Examiner*—Jeffery Hofsass
*Assistant Examiner*—Lam Pham
(74) *Attorney, Agent, or Firm*—Frishauf, Holtz, Goodman & Chick, P.C.

(57) ABSTRACT

Disclosed is a portable gas alarm device easy to be fabricated as a small-sized one handy to carry and high in convenience for use. The portable gas alarm device comprises a gas alarm device body having a casing flat in whole and a fitting member provided on the casing to fit it to the human body. The gas alarm device body has a control circuit board extending to the direction of the flat plane of the casing, a display mechanism is arranged in a central area on the front surface side of the control circuit board, a gas sensor and an alarm buzzer are arranged on the right and left sides of the display mechanism, and a battery fitting chamber is provided on the back surface side of the circuit board. A vibration generator for alarm may be provided in the gas alarm device body. The fitting member may be one suitable for use in fitting the gas alarm device body to a person's wrist or a person's wear.

9 Claims, 1 Drawing Sheet

PORTABLE GAS ALARM DEVICE

BACKGROUND OF THE INVENTION

1. Field of the Invention

The present invention relates to a portable gas alarm device.

2. Description of the Background Art

There are generally frequent occasions when it may be possible in, for example, underground job sites or gateways, or other places where persons enter, or working regions that air in an environmental atmosphere is in a dangerous state, or will become a dangerous state, such as occasions when a harmful gas or gases such as carbon monoxide gas and hydrogen sulfide gas may possibly be contained in air in such an environment, or when the oxygen gas concentration in air may possibly be lowered.

When the air in the environmental atmosphere has become a dangerous state to persons due to high concentration of the harmful gases contained or low oxygen gas concentration, it is necessary to detect the situation.

From such a demand, there have heretofore been proposed various types of portable gas alarm devices. Since the conventional portable gas alarm devices are generally large in size, however, they are fabricated as, for example, shouldering type and involve problems that they are considerably unhandy to carry and are being a great obstacle to practice the intended work or the like.

SUMMARY OF THE INVENTION

The present invention has been completed on the basis of the foregoing circumstances and has as its object the provision of a portable gas alarm device which is easy to be fabricated as a small-sized one handy to carry and high in convenience for use.

According to the present invention, there is thus provided a portable gas alarm device comprising a gas alarm device body having a casing flat in whole and a fitting member provided on the casing to fit it to a human body of a person, wherein the gas alarm device body has a control circuit board provided so as to extend to the direction of the flat plane of the casing inside the casing, a display mechanism is arranged in a central area on the front surface side of the control circuit board, a gas sensor and an alarm buzzer are arranged on the right and left sides of the display mechanism, and a battery fitting chamber is provided on the back surface side of the circuit board.

In the above-described construction, a gas sensor holding part for holding the gas sensor and an alarm buzzer holding part for holding the alarm buzzer may preferably be formed on surface portions of the casing of the gas alarm device body in a state projected upper than the surface of the central area in which the display mechanism is arranged.

A light emitting part for alarm and at least one operating button may preferably be provided on the upper and lower sides of the display mechanism on the front surface side of the control circuit board in the gas alarm device body. A vibration generator for alarm may preferably be provided in the gas alarm device body.

The concentration of a gas detected, time and a life of a battery fitted in the battery fitting chamber may be displayed in the display mechanism of the gas alarm device body.

The gas sensor may be held detachably in the gas sensor holding part in the casing of the gas alarm device body so as to be interchangeably.

The fitting member may preferably be one suitable for use in fitting the gas alarm device body to a person's wrist or in fitting the gas alarm device body to a person's wear.

In the above construction, one selected from among an oxygen gas sensor, hydrogen sulfide gas sensor and a carbon monoxide gas sensor may preferably be used as the gas sensor.

According to the above-described construction, the gas sensor and alarm buzzer are arranged respectively in areas on both right and left sides of the central area, in which the display mechanism is arranged, on the front surface side of the control circuit board arranged in the casing, and the battery fitting chamber is provided on the back surface side of the control circuit board, whereby the parts relatively great in area or volume among the essential component parts for the gas alarm device are rationally arranged, so that the gas alarm device body can be constructed into a small-sized and thin-walled one as a whole, and moreover the fitting member is provided in the gas alarm device body, so that a portable gas alarm device having actually high convenience is provided.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE PREFERRED EMBODIMENTS

The embodiments of the present invention will hereinafter be described in detail.

Figure 1:
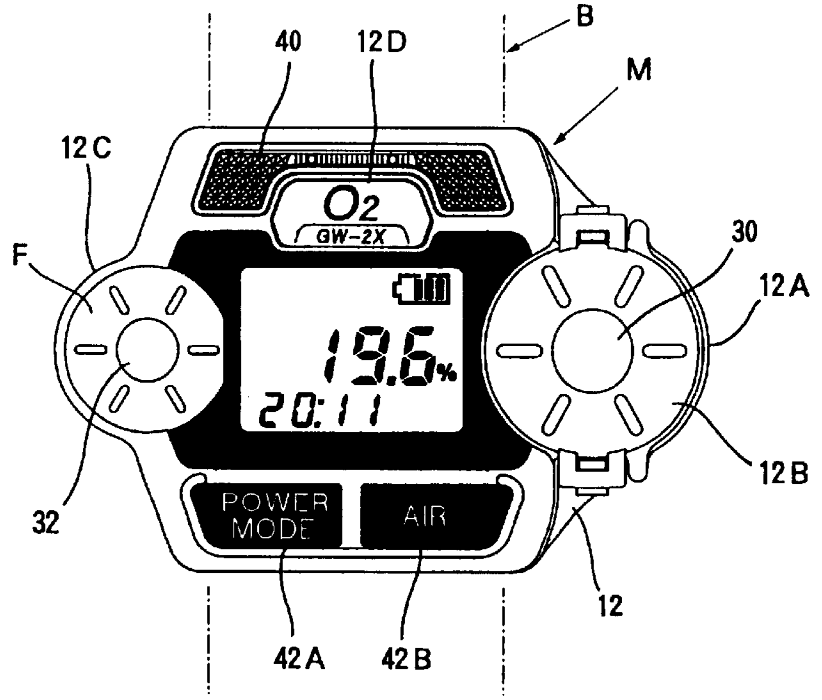
FIG. 1 is a front elevation of a portable gas alarm device according to the present invention viewed from the front surface side thereof.
Figure 2:
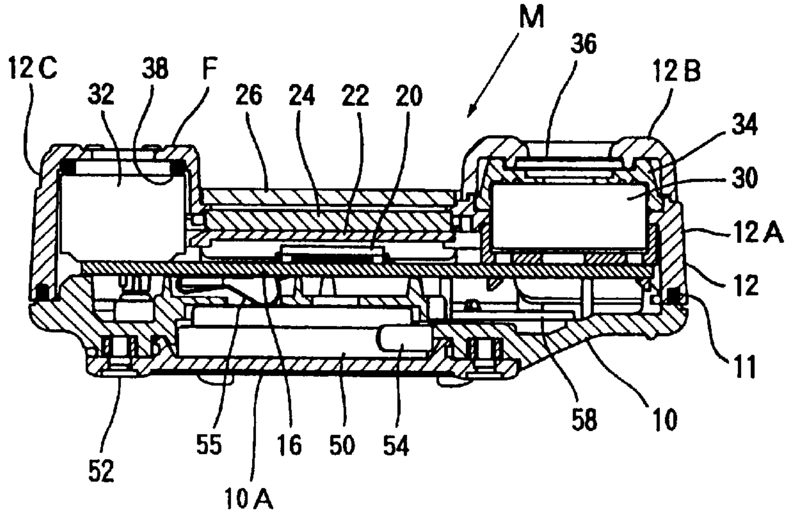
FIG. 2 is a sectional view illustrating the portable gas alarm device in FIG. 1.

FIG. 1 is a front elevation of a portable gas alarm device according to the present invention viewed from the front surface side thereof, and FIG. 2 is a sectional view illustrating the portable gas alarm device.

This portable gas alarm device is essentially constructed by a gas alarm device body M and a fitting member B provided on the gas alarm device body M to fit it to a human body. In an embodiment illustrated in FIG. 1, the fitting member B is composed of a wristwatch type fitting member, specifically, the same belt as that for a wristwatch.

As illustrated in FIG. 2, the gas alarm device body M is equipped with a casing flat in whole, which is composed of a back-side casing member 10 and a front-side casing member 12 joined and fixed to the back-side casing member 10 by a plurality of screws (not illustrated) through a ring-like packing 11. A control circuit board 16 in the form of a flat plate is provided in the casing in a state held by the back-side casing member 10 and the front-side casing member 12 fixed to each other and in a state extending to the direction of the flat plane of the casing.

On the surface of the control circuit board 16, a central processing unit 20 is mounted at a central part thereof, and various necessary function elements are mounted. A light guide plate 22 is provided so as to cover an upper portion of a space including the central processing unit 20, and a panel-like display mechanism 24 composed of a liquid crystal display panel is arranged on the light guide plate 22. A protective window plate 26 is arranged above this panel-like display mechanism 24, and a back light composed of light emitting diodes (not illustrated), which emit light to the panel-like display mechanism 24 through the light guide plate 22, is provided.

The above-described light guide plate 22, panel-like display mechanism 24 and window plate 26 are all held and fixed by a holding part of the front-side casing member 12.

As illustrated in FIG. 1, on the front surface side of the control circuit board 16, a gas sensor 30 is arranged in the right area of the central area, in which the panel-like display mechanism 24 is arranged, and moreover an alarm buzzer 32 is arranged in the left area of the central area. These members are held by their corresponding holding parts formed in the front-side casing member 12.

More specifically, a cylindrical sensor casing part 12A opening at its upper end in FIG. 2 is formed in the right area of the front-side casing member 12, and the columnar gas sensor 30 contained in this casing part is held in a state fixed through a sensor packing 34 by a sensor cap 12B detachably fitted on the sensor casing part 12A, whereby the gas sensor 30 is detachably fixed and may be interchanged without separating the front-side casing member 12 from the back-side casing member 10 in the casing. Reference numeral 36 indicates a gas-permeable waterproof sheet composed of, for example, polytetrafluoroethylene.

As the gas sensor 30 in the present invention, any gas sensor element may be used according to the kind of the objective gas to be detected. As examples thereof, may be mentioned a galvani type gas sensor element for detecting oxygen gas, a controlled potential electrolysis type gas sensor element for detecting carbon monoxide gas, and a controlled potential electrolysis type gas sensor element for detecting hydrogen sulfide gas.

On the other hand, a cylindrical buzzer holding part 12C having an inner circumferential flange F at its upper end in FIG. 2 is formed in the left area of the front-side casing member 12, and the alarm buzzer 32 is arranged in a state contained in the buzzer holding part 12C so as to be located on the surface of the control circuit board 16 in the state fixed to the casing, and thereby held between the control circuit board 16 and the inner circumferential flange F. Reference numeral 38 designates a ring-like packing.

In the front-side casing member 12, the gas sensor holding part composed of the sensor casing part 12A and the sensor cap 12B and the buzzer holding part 12C are in the state projected upward from the level of the window plate 26 of the panel-like display mechanism 24 in FIG. 2.

On the front surface side of the control circuit board 16, a light emitting part 40 for alarm composed of a light source consisting of light emitting diodes (not illustrated) provided at left and right positions in an upper area of the panel-like display mechanism 24 in FIG. 1 and a glass plate for light emitting part held by the front-side casing member 12 so as to cover light source is arranged, and operating buttons are provided in a lower area of the panel-like display mechanism 24. In the embodiment illustrated in FIG. 1, a first operating button 42A combining a main switch with a mode changing switch, on which "POWER" and "MODE" are displayed on 2 lines, and a second operating button 42B for controlling a function to change an alarm generating standard according to the kind of the gas sensor 30, i.e., the kind of the objective gas to be detected by the gas sensor 30, on which "AIR" is displayed, are arranged on left and right sides, respectively.

In an area between the light emitting part 40 for alarm and the panel-like display mechanism 24, a vibration generator (not illustrated) for alarm composed of a vibrating motor is provided on the surface of the control circuit board 16. Reference character 12D designates a part holding the vibration generator for alarm formed in the front-side casing member 12, and a display "$O_2$" indicating the kind of the objective gas to be detected is made at top surface thereof by, for example, sticking a label.

On the back surface side of the control circuit board 16 on the other hand, a battery fitting chamber is defined by the control circuit board 16 itself and the back-side casing member 10, and the so-called button type battery 50 is fitted therein. A cover plate 10A is detachably attached by fitting screws 52 to the back-side casing member 10 at an opening part of the battery fitting chamber, whereby the battery 50 can be interchanged.

Reference numerals 54 and 55 designate a plus side contact plate and a minus side contact plate, respectively, whereby a current from the battery is supplied through the control circuit board 16 as operating current for each operating part. Reference numeral 58 indicates a board for limiting resistor.

The control circuit board 16 is provided with an electronic circuit having a function of controlling the operation in each operating part of the gas alarm device body M, and the operations of the panel-like display mechanism 24, gas sensor 30, alarm buzzer 32, light emitting part 40 for alarm, vibration generator for alarm and other operation mechanisms are conducted and controlled by this control circuit board 16.

The operation of the portable gas alarm device of the above-described construction will be described.

When the first operating button 42A is operated under the state that the battery 50 has been fitted in the battery fitting chamber, to make the gas alarm device member M operate so that the gas sensor 30 and the panel-like display mechanism 24 become an operated state.

In this state, air in an environmental atmosphere diffuses to reach the gas sensor 30, so that the concentration of the intended gas is detected, and the result thereof is displayed on the panel-like display mechanism 24.

In the panel-like display mechanism 24 according to the embodiment illustrated in FIG. 1, the residual quantity of electricity in the battery 50 is displayed as an image on the upper line, the concentration (concentration of oxygen gas ($O_2$) in this embodiment) of the gas detected is displayed as a numerical value on the medium line, and the present time is displayed on the lower line according to a signal from a timer circuit in the central processing unit 20. However, it may not be necessary to make these displays at the same time, and it is also possible to construct the panel-like display mechanism 24 in such a manner that these items are successively displayed automatically or by a manual operation, in the present invention. It is further possible to construct the panel-like display mechanism 24 in such a manner that other information is displayed additionally.

The concentration of the gas detected by the gas sensor 30 is sent to the central processing unit 20 as a current signal or voltage signal to be processed, whereby an alarm actuating signal is outputted when the concentration of the objective gas to be detected exceeds the preset reference value, and an alarm annunciating mechanism is driven thereby to raise an alarm.

For example, when the objective gas to be detected is oxygen gas, the reference value is determined to be 18% by way of example, and an alarm actuating signal is outputted when the concentration becomes a value lower than this reference value. The reference value is determined to be 10 ppm by way of example when the objective gas to be detected is hydrogen sulfide gas, while the reference value is determined to be 50 ppm by way of example when the objective gas to be detected is carbon monoxide gas. An alarm actuating signal is outputted when the concentration exceeds each reference value.

In the illustrated embodiment, the alarm buzzer 32, light emitting part 40 for alarm and vibration generator for alarm are provided as alarm annunciating mechanisms, and an alarm is raised by buzzer sound, light emission and vibration, respectively.

When plural kinds of alarm annunciating mechanisms are provided as described above, it is not necessary to drive all the alarm annunciating mechanisms at the same time, and it is preferable to conduct a cyclic alarm operation whereby the respective alarm annunciating mechanisms are successively driven only for a predetermined period of time respectively. According to such drive control, the consumption of the battery 50 can be inhibited compared with the case where the alarm annunciating mechanisms are driven at the same time.

The gas alarm device body M is fitted on, for example, a person's wrist by the fitting member B and carried together with its body of the person. Accordingly, when the environmental atmosphere of the person becomes a dangerous state due to high concentration of the dangerous gas contained or low oxygen gas concentration, that effect is annunciated by the display of the panel-like display mechanism 24, and light emission of the panel-like display mechanism 24, buzzing of the alarm buzzer 32 and operation of the vibration generator for alarm. Accordingly, the person can immediately make information, take proper protective means, or take some counter measure such as evacuation from such a site.

According to the portable gas alarm device of the present invention, the battery fitting chamber is provided on the back surface side of the control circuit board 16 in the gas alarm device body M, the button type battery 50 is fitted therein, and moreover on the front surface side of the control circuit board 24, the panel-like display mechanism 24 is provided at the central area, and the gas sensor 30 and the alarm buzzer 32, which are both in a columnar form are arranged on both right and left sides thereof, whereby the parts great in occupied volume among the parts making up the gas alarm device are rationally arranged taking their volumetric sizes into consideration, so that the parts can be contained in the casing flat in whole to miniaturize the device as a whole because useless spaces are scarcely present. In particular, the use of a columnar shaped gas sensor 30 and buzzer 32 permits making both right and left sides of the casing round, so that the device is safe for the user thereof.

With respect to the dimensions of the respective parts in the gas alarm device body M according to the illustrated embodiment, a maximum length in a horizontal direction in the elevation of FIG. 1 is about 65 mm, a maximum length in a vertical direction is about 43 mm, a thickness of the portion, in which the panel-like display mechanism 24 is located, is about 18 mm, a thickness of the gas sensor holding part is about 24 mm, and a thickness of the portion of the alarm buzzer holding part 12C is about 22 mm.

Accordingly, when the fitting member B composed of, for example, a fitting member for wristwatch is provided, the gas alarm device body M can be carried by fitting it on a person's wrist, so that great convenience is achieved as a portable gas alarm device.

When the gas alarm device body M is fitted on a person's wrist, it is preferable that the device be fitted in a state that the gas sensor 30 is located at the position near the tip of the hand. In this case, the gas sensor 30 is in a state almost exposed from the edge of a sleeve of a wear of the person, so that a situation that air in an environmental atmosphere surely reaches the gas sensor 30 is ensured.

In the above-described embodiment, the gas sensor holding part and the buzzer holding part 12C are in the state projected upward from the level of the panel-like display mechanism 24 in the casing, so that the panel-like display mechanism 24 is prevented from being damaged by its contact with an external object.

Although the portable gas alarm device according to the present invention has been described centering an embodiment thereof, various changes and modifications may be added thereto.

For example, on the front surface side of the control circuit board 16 in the gas alarm device body, it is only necessary to arrange the gas sensor and the alarm buzzer on both right and left sides of the display mechanism, and other parts or members may be freely positioned. On the back surface side of the control circuit board 16, the construction is free so far as the battery fitting chamber is provided.

The fitting member is not limited to the fitting member for wristwatch, and may be in any other form or may have other functions. The fitting member may be one capable of being fitted to a person's wear, not direct to a person's body. Examples thereof include a clip and a pin. The fitting member may be formed integrally with the casing according to the form thereof.

The fitting member may be formed in an easily interchangeable shape.

According to the above-described construction, the parts relatively great in area or volume among the essential component parts for the gas alarm device such as the gas sensor and alarm buzzer as well as the battery fitting chamber are rationally arranged, so that the gas alarm device body can be constructed into a small-sized and thin-walled one as a whole, and moreover the fitting member is provided in the gas alarm device body, so that a portable gas alarm device having actually high convenience is provided.

What is claimed is:

1. A portable gas alarm device comprising:

a gas alarm device body comprising a substantially flat casing;

a fitting member provided on the casing for fitting the gas alarm device body to a human body;

a control circuit board provided inside the casing and extending in a direction of a flat plane of the casing;

a display mechanism arranged in a central area of the casing on a front surface of the control circuit board;

a gas sensor and an alarm buzzer each arranged on one of a right side and a left side of the display mechanism; and a battery fitting chamber provided on a back surface of the circuit board;

wherein a gas sensor holding part and an alarm buzzer holding part are formed on surface positions of the casing projecting above the central area in which the display mechanism is arranged; and wherein a light emitting part for alarm and at least one operating button are provided on upper and lower sides of the display mechanism on a front surface side of the control circuit board in the gas alarm device body.

2. The portable gas alarm device according to claim 1, wherein the display mechanism displays a concentration of a gas detected, time and a life of a battery fitted in the battery fitting chamber.

3. The portable gas alarm device according to claim 1, wherein the gas sensor is held detachably in the gas sensor holding part in a manner such that the gas sensor is interchangeable.

4. The portable gas alarm device according to claim 1, wherein the fitting member is adapted to fit the gas alarm device body to a user's wrist.

5. The portable gas alarm device according to claim 1, wherein the fitting member is adapted to fit the gas alarm device body to a user's clothing.

6. The portable gas alarm device according to claim 1, wherein the gas sensor is selected from among an oxygen gas sensor, a hydrogen sulfide gas sensor and a carbon monoxide gas sensor.

7. The portable gas alarm device according to claim 1, wherein both the gas sensor and the alarm buzzer have a columnar shape such that both right and left sides of the casing are round.

8. The portable gas alarm device according to claim 1, wherein a vibration generator for alarm is provided in the gas alarm device body.

9. The portable gas alarm device according to claim 8 wherein the gas sensor is adapted to detect an alarm condition, and wherein the alarm buzzer, the light emitting part and the vibration generator are each independently successively operated for a predetermined period of time in a cyclic alarm operation when the alarm condition is detected.

* * * * *